United States Patent
Boese et al.

(10) Patent No.: US 7,578,787 B2
(45) Date of Patent: Aug. 25, 2009

(54) CATHETER DEVICE

(75) Inventors: Jan Boese, Eckental (DE); Martin Kleen, Neunkirchen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 401 days.

(21) Appl. No.: 11/040,468

(22) Filed: Jan. 21, 2005

(65) Prior Publication Data
US 2005/0228274 A1    Oct. 13, 2005

(30) Foreign Application Priority Data
Apr. 13, 2004    (DE) .................. 10 2004 017 834

(51) Int. Cl.
*A61B 1/00* (2006.01)
*A61M 31/00* (2006.01)
*A61M 25/00* (2006.01)

(52) U.S. Cl. .................. 600/152; 604/95.03; 604/525; 604/528; 600/144; 600/145

(58) Field of Classification Search .......... 600/300, 600/585, 139–152; 604/19, 48, 93.01, 144–146, 604/117, 150, 424, 435, 437, 443, 523–528, 604/95.04
See application file for complete search history.

(56) References Cited

U.S. PATENT DOCUMENTS

| | | | | |
|---|---|---|---|---|
| 4,292,961 A | * | 10/1981 | Kawashima | ................ 600/145 |
| 5,662,587 A | * | 9/1997 | Grundfest et al. | ........... 600/114 |
| 6,468,203 B2 | * | 10/2002 | Belson | ...................... 600/146 |
| 2003/0065250 A1 | * | 4/2003 | Chiel et al. | ................. 600/115 |
| 2004/0068161 A1 | * | 4/2004 | Couvillon, Jr. | .............. 600/143 |
| 2004/0147837 A1 | * | 7/2004 | Macaulay et al. | ........... 600/424 |

* cited by examiner

Primary Examiner—Nicholas D Lucchesi
Assistant Examiner—Victoria P Campbell

(57) ABSTRACT

Catheter device, comprising a catheter (2) for introduction into a hollow organ, especially a vessel, with a number of bending elements (12, 12a-12f, 12a'-12e') arranged around the longitudinal axis of the catheter and distributed over at least a part of the catheter length, which can be activated separately for a specified change of shape via a control device (5), as well as a number of bending sensors (15, 15a-15e, 15a'-15e') arranged around the longitudinal axis of the catheter and distributed over at least a part of the catheter length communicating with a control device (5), with the control device (5) being embodied to determine the given geometrical shape of the catheter (2) on the basis of the bending sensor signals and to determine the change of shape of the bending elements (12, 12a-12f, 12a'-12e') necessary for a movement of the catheter (2) by a forward movement length preferably specifiable on the user side to enable the catheter (2) to move by itself at least in part, by explicit bend-dependent force application to the wall of the organ (16).

11 Claims, 4 Drawing Sheets

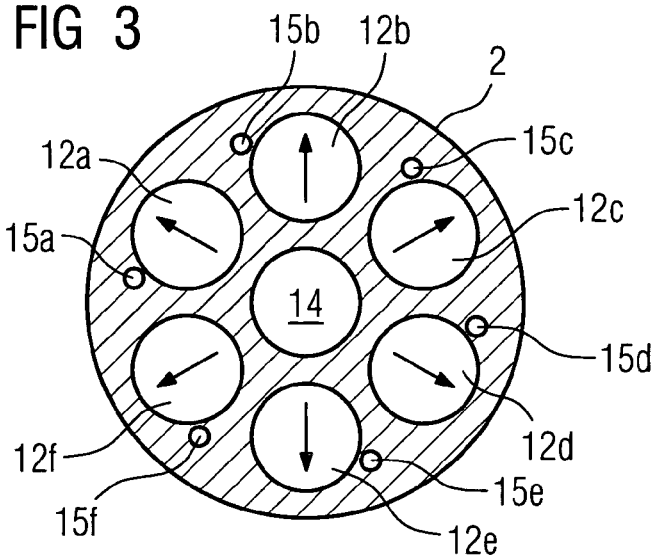
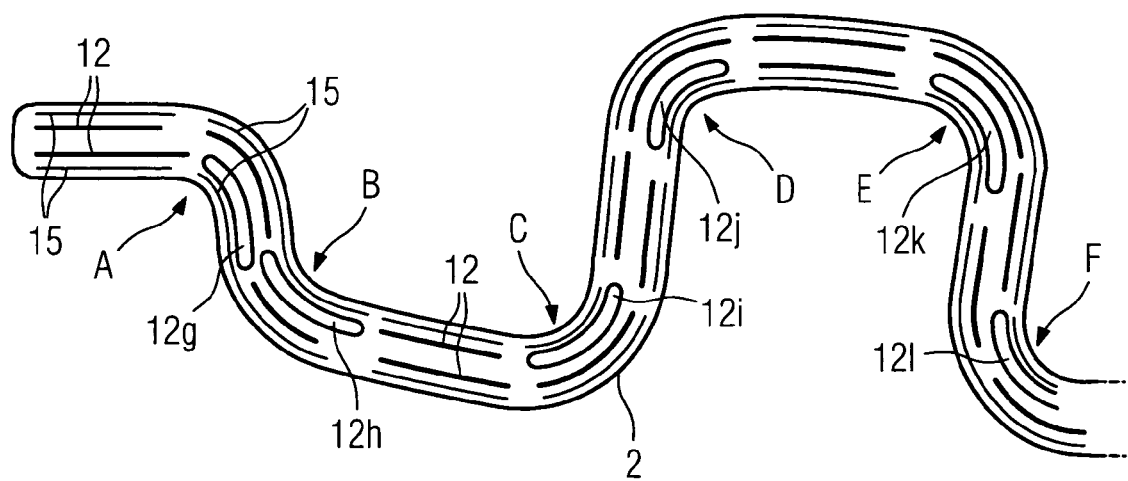

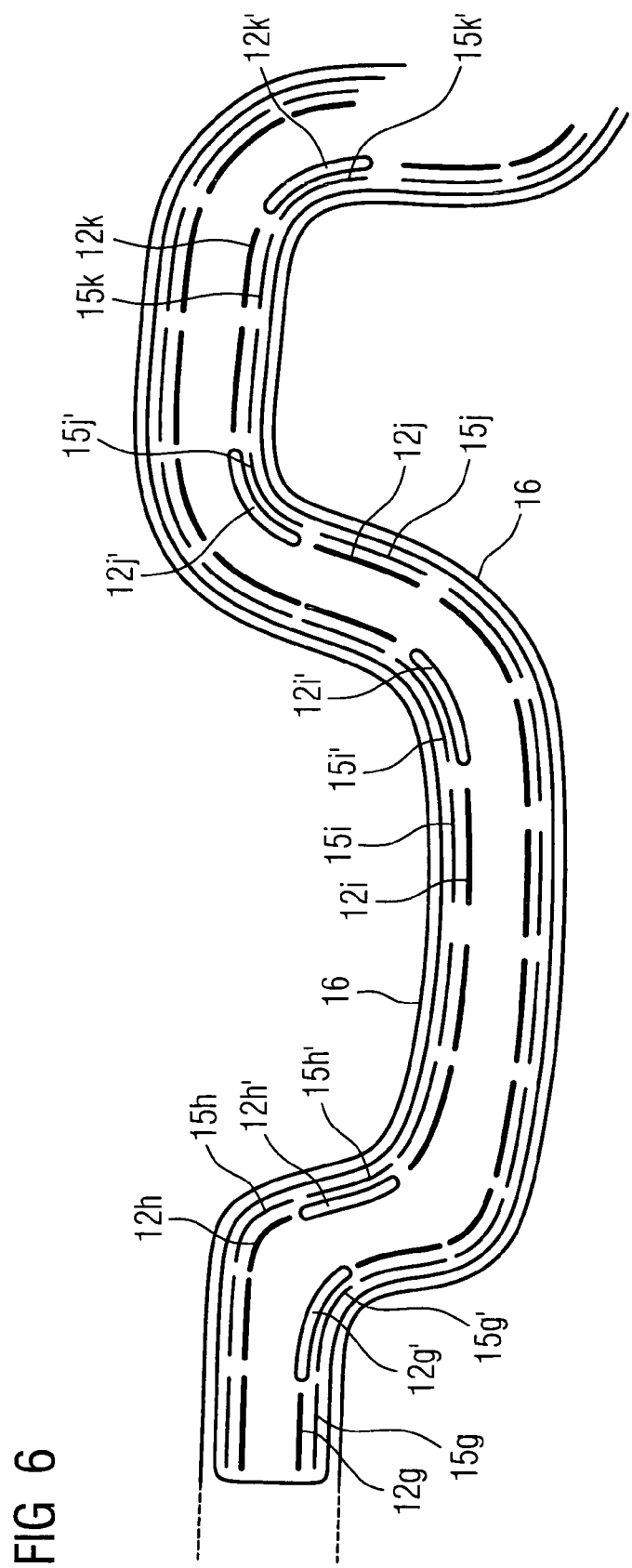

CATHETER DEVICE

CROSS REFERENCE TO RELATED APPLICATIONS

This application claims priority to the German application No. 10 2004 017 834.8, filed Apr. 13, 2004 which is incorporated by reference herein in its entirety.

FIELD OF INVENTION

The invention relates to a catheter device, comprising a catheter for introduction into a hollow organ, especially a vessel.

BACKGROUND OF INVENTION

Catheters, a term which also covers endoscopes in this document, are being increasingly used for intravascular or intercardial treatment, with applications in the gastro-intestinal tract also being possible. To this end the catheter is introduced into the elongated hollow organ, and, following the shape of the organ, it has to negotiate multiple curves in the vessel or the intestine. Following the curves is made easier by making the catheter relatively flexible. This flexibility however makes it more difficult to push the catheter forward manually since such a catheter is as a rule advanced by the doctor from outside the patient. With multiple curves the pushing force is used up in adapting the shape of the catheter, which means that where there are curves in the organ, the catheter bends ever more and de facto it no longer moves forward. Simultaneously, the deformation of the catheter has the effect of expanding the walls of the organ which causes pain and also brings the danger of injury. To achieve any advance at all, particularly for any catheter that is inserted a relatively long way into an organ, essentially far more force has to be expended to move it forward and applied than would actually be necessary if the catheter were able to follow the forward movement force without "losses".

SUMMARY OF INVENTION

The result of this problem is that specific areas cannot be reached with a catheter, whether it is a normal catheter which for example features a particular function mechanism at its tip, e.g., for stimulation or for boiling away of tissue or for conducting electrical signals, or whether it is an endoscopic catheter. Thus, for example, only a small part of the small intestine can be reached and this can only be done with significant difficulties. Another problem is the introduction of a catheter through the aorta and the heart chambers into the left ventricle, involving significant disturbances to the heart rhythm and danger of injury.

To reduce the resistance which arises especially in the area of the catheter tip primarily at points where the organ bends, designing catheters to deform using wire sections at the tip is known. Here, however, it is only ever the farthest end which is actively deformable, the rest of the length of the wire-tip controlled catheter, no matter what variant, can be designed to have any degree of stiffness or flexibility but is not actively deformable. Arranging a magnet on the tip of the catheter is also known so that the alignment of the tip can be adjusted magnetically from outside and the tip can thus be navigated magnetically. However, this process too still requires force to be transferred from the end of the catheter distant from the body over the length of the catheter to the tip, to guarantee the forward movement of the instrument in the body.

From the subsequently published German Patent Application DE 102004003082.0 a catheter is known which can be actively locally deformed over at least part of its length. This is made possible by integration of bending elements which allow the shape to be changed in a defined way by suitable activation. It allows this catheter to actively adapt itself to the given shape of the organ, that is for the anatomical shape of the organ to be simulated in the catheter. This allows the shape of the catheter to be almost continuously adapted to the shape of the vessel during the forward movement, so that, seen locally, the resistance presented by the organ to the catheter as it moves forward is reduced. Here, too, the catheter is always advanced manually, the only "driving" force is the forward movement force initiated by the doctor.

An object of the invention is to specify a catheter device which at least in part allows the catheter to move of its own accord.

This object is achieved by the claims.

To resolve this problem an inventive catheter device is provided, comprising a catheter for induction into a hollow organ, especially a vessel, with a number of bending elements arranged around the longitudinal axis of the catheter and distributed over at least part of the length of the catheter, separately controllable for a predefined change of shape, as well as a number of bending sensors arranged around the lengthwise axis of the catheter and distributed over at least a part of the catheter length, communicating with the control device, with the control device being used to determine the given geometrical shape of the catheter on the basis of the bending sensor signals and for determining the required change of shape of the bending elements for a movement of the catheter by a user-side specifiable length of forward movement, which is embodied to enable an at least partly self-powered movement of the catheter by explicitly exercising a bending-dependent force on the organ wall.

The inventive catheter device is based on a catheter the shape of which can be actively changed or adjusted over a part of its length, such a device being described for example in the subsequently published German Patent Application DE 102004003082.0. The bending elements integrated on the catheter side are also assigned correspondingly distributed bending sensors which also communicate with the control device. On the basis of the sensor signals the control device is able to compute the actual shape of the catheter at the moment that the signals are recorded. Each sensor delivers a signal depending on its shape or deformation in relation to an initial shape, on the basis of which the shape of the catheter in the area of the sensor can be deduced. After the position of the sensors and also that of the bending elements both in relation to a catheter cross section and the catheter length is known, an at least two-dimensional imaging of the precise geometrical shape of the catheter can be determined.

If the user now specifies a length of forward movement for the catheter which can be done in different ways, as is described below, the control device is able, taking account of the actual geometry of the catheter as well as the known length of forward movement, to determine how a number of the bending elements or all of them are to be controlled, by explicitly exercising a local force through the change of shape on the wall of the organ or vessel, which causes the catheter to move forward in the organ by slight deformation of the vessel or organ wall. The catheter can thus move by itself, meaning that by corresponding activation of the bending elements the catheter moves or "crawls" forward by explicitly changing its shape. In the ideal case the catheter is also in a position to move or be introduced on its own into the organ.

In this case it is especially useful if all the bending elements to be deformed for moving the catheter are able to be simultaneously activated. This means that there is a largely simultaneous and even change of shape of the relevant bending elements over the inserted catheter length. The shape can in this case be changed continuously or in steps from the actual shape or target shape which is computed as a function of the given length of forward movement, in which case the change of shape should be undertaken relatively slowly to avoid the force being exercised too quickly on the organ wall. The curvature of the anatomy remains almost static in this case, regardless of the relatively slight deformation for "supporting" the catheter especially in the area of the curvature. When the adapted curves of the device move along the longitudinal axis of the catheter during the change of shape, the catheter exercises a force on the wall of the organ at many points of which the number in the final analysis depends on the number of curves, for example, of the vessel or of the intestine. The force to move the device along the longitudinal axis is thus transmitted at many different positions on the organ wall. This means that at no point on the wall is the force so high as to cause pain or produce the danger of a perforation. The energy entered, namely the energy necessary to change the shape, is used almost exclusively to advance the device, apart from the proportion of the energy absorbed as a result of its slight deformation. This active self-movement of the catheter particularly advantageously allows regions of the body to be made accessible which were previously not accessible with a catheter, either an operational catheter or an endoscopy catheter, or were only accessible at high risk.

The specification for the calculated change in shape and thereby the deformation length needed to determine the control parameters of the individual bending elements can be different. According to a first inventive embodiment the pre-specified length of forward movement can be specified as an absolute value via the input means of the control device. The doctor thus defines, before or after introducing the catheter, a length L, for example 2 cm or 5 cm, by which he wishes the catheter to actively move forward in one step in each case. This means that a movement increment is thereby defined, on which each step-by-step movement cycle is based. Such a movement cycle can be faster or slower, depending on how quickly the elements can react or how quickly the system is designed to be within the framework of the activation. The faster the bending elements react, the more fluid is the step-by-step movement, with a rapid change of shape being linked to a higher energy or force application on the wall of the vessel. The corresponding design should be produced here depending on the area of application.

Alternatively to direct entry of the movement increments or of a length of forward movement via a defined absolute value, for example, there is the option of defining the length of forward manually by moving the catheter, said movement being able to be recorded for determining the length of forward movement using a recording means. This means that the doctor defines during the first insertion movement, using a corresponding input means, e.g., a movement recorder with high resolution, the amount of forward movement on which the steps by which the device will move under its own power are based. It is also conceivable, to move a catheter mechanically using a motor-driven advancing mechanism, in which case the amount of forward movement would have been defined via the corresponding motor parameters. In this case it is also conceivable, instead of determining the amount of forward movement via an active start-stop movement, to define the length of forward movement as the length by which the catheter is moved manually within a specifiable time interval for example. If this time interval, for example, amounts to two seconds and if during this time the catheter is moved forward by 4 cm, then this is the length of forward movement determined. This inventive embodiment also has the advantage that the doctor can almost continuously move the catheter forward, as well, with a sufficiently short time interval being selected and at the end of each time interval the active element activation being calculated in respect of the length of forward movement recorded immediately beforehand and the corresponding activation being performed. The doctor thus operates in a manual support role here, with, as a result of the continuous very fast active change in shape in connection with the active wall support, the problems arising from the activity of moving the catheter forward manually, as produced by the prior art, not occurring here since any spreading resulting from a manual advance is immediately reduced.

Basically it is possible for the doctor to perform only one active movement step in each case, meaning that, on the basis, for example, of the entered absolute value the change in shape is calculated once and the corresponding activation is initiated for active forward movement. He can thus, for example, almost feel his way forward in steps and trace the approach to his target area via an x-ray check or the like. Alternatively, to single-step movement initiated by the doctor it is conceivable, for example, using a given absolute value, for the control device to calculate the necessary change in shape of the bending elements for a multiple movement of the catheter using the one prespecified length of forward movement value in each case multiply in succession and to activate the bending elements accordingly. The length of forward movement is thus specified only once and forms the basis of each step calculated. Naturally there is the option of stopping the "crawling mode" at any time or changing the incremental length of forward movement value.

Since, as explained, the active interaction of the catheter with wall of the organ on active deformation of the catheter is accompanied by a certain deformation of the organ, depending on the size of the bend-dependent force initiated locally, an advantageous development of the invention makes provision for the control device to be embodied for activating the bending elements such that the catheter, once a movement is ended, again essentially assumes the geometrical shape which it had before the movement. This means that after each movement step or after each forward movement by the defined movement increment the bending elements are preferably activated over the entire length of the catheter so that the catheter takes the shape that it had before this movement step, said shape corresponding almost exactly to the anatomy of the organ. Any deformations of the organ after each step are thus corrected again so that they do not build up gradually with a continuous step-by-step movement. This "shape adaptation" is possible in any event since the shape assumed is checked continuously via the bending sensors and can be compared with the shape assumed beforehand. Since the position of the sensors as well as of the bending elements is known over the length of the catheter, it is possible to calculate which sensor must be lying correctly relative to the preceding actual shape and which signal it must deliver so that the catheter again emulates the previous vessel anatomy.

BRIEF DESCRIPTION OF THE DRAWINGS

Further advantages, features and details of the invention are obtained from the exemplary embodiment described below as well as on the basis of the diagrams. The diagrams show.

DETAILED DESCRIPTION OF INVENTION

Figure 1:
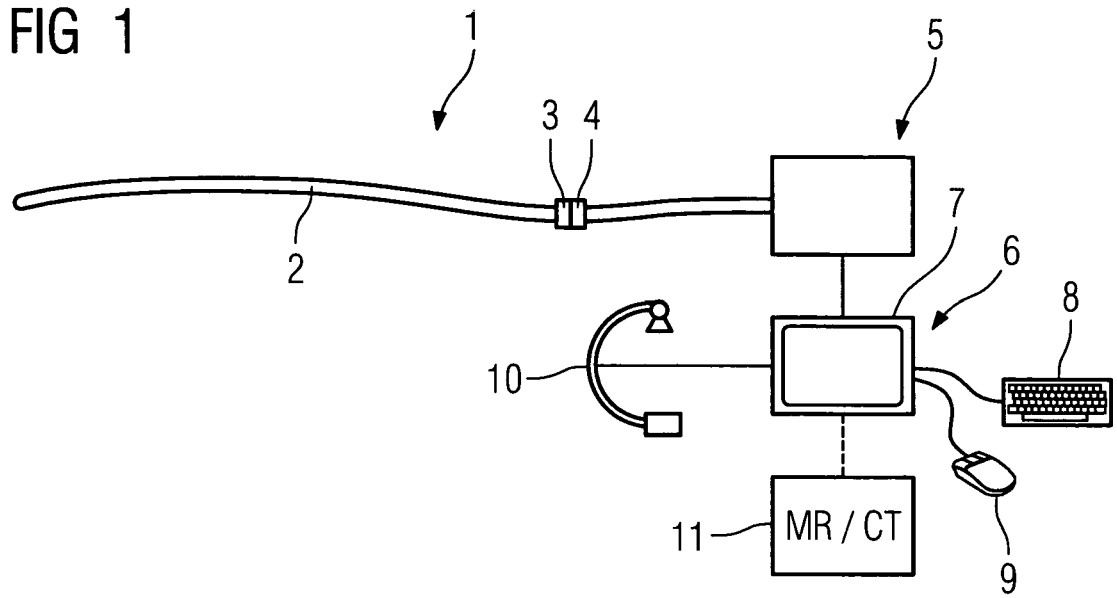
FIG. 1 a sketch showing the principle of the inventive catheter device.

FIG. 1 shows an inventive catheter device 1 comprising a catheter 2, at the free end of which, the end which is not to be introduced into the patient, a connection device 3 is provided, which is coupled with a connection device 4, which can be controlled by a control device 5, via which the bending elements integrated into the catheter can be controlled. It is possible via control device 5 to activate each individual bending element separately. The bending elements which are arranged distributed along the lengthwise axis of the catheter and along the catheter length are, for example, tubular hollow bodies to which a liquid or gaseous filler medium can be hydraulically or pneumatically applied, which in their non-loaded state are unfilled and flexible and in their filled state under pressure assume a prespecified relatively rigid shape. These make it possible to bend the catheter explicitly as described in greater detail below. The control device 5 is linked to an input device 6, comprising a monitor 7, a keyboard 8 and also a mouse 9. The operator can use this device, talking into consideration an image on the monitor 7, supplied in parallel, for example, by an x-ray image taken during invasion with an x-ray device 10 or where necessary using an image data set for example from magnetic resonance or computer tomography 11, to specify the direction in which the catheter is to be bent on the tip side by corresponding activation of one or more image elements provided there, in order to allow simple navigation.

The functional principle is based on the fact that a plurality of bending elements are integrated into the catheter and that these can be moved to form a particular shape when pressure is applied within them.

Figure 2:
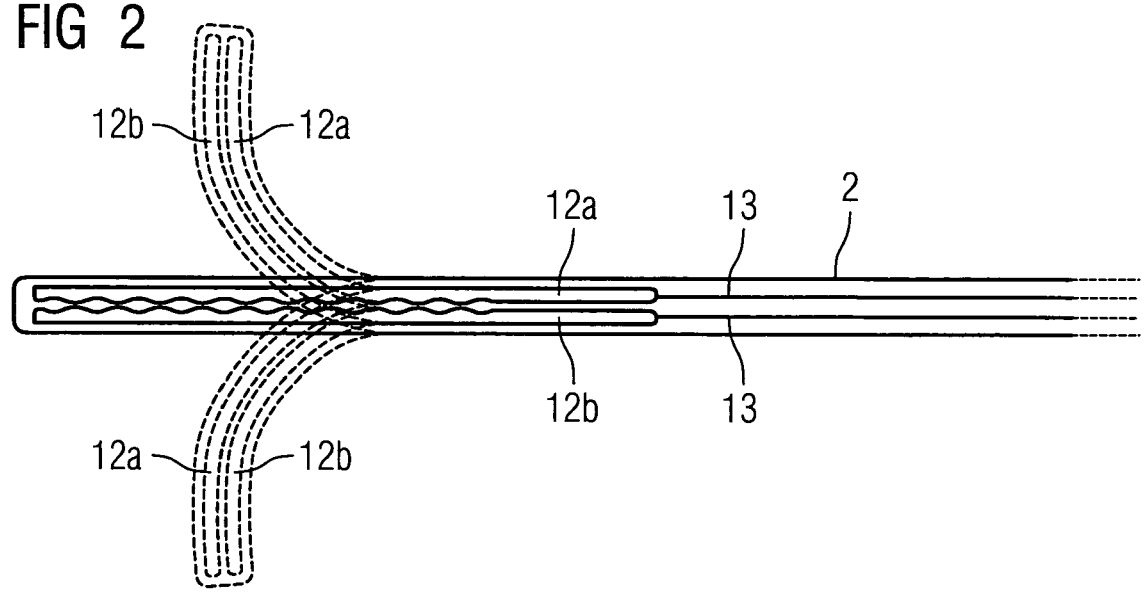
FIG. 2 a diagram of a part of the catheter with two bending elements operating in opposite directions, FIG. 3 cross sectional view through a catheter with a number of offset, distributed bending elements and bending sensors arranged radially outwards, FIG. 4 a diagram of the progress of a catheter obtained by activating various bending elements, and FIGS. 5 and 6 sketches showing the principle of the inventive catheter device to illustrate the functional sequence of movement under its own power.

FIG. 2 shows a basic diagram of two bending elements 12a, 12b integrated into the catheter 2, both embodied in the shape of a hose and which can, for example, be made of an inelastic plastic material, e.g. PUR or PTFE or of any other plastic. Each bending element 12a, 12b has a shorter wall section on one side and a longer wall section on the opposite side, meaning that its walls are unsymmetrical. If a filler medium, for example water, saline solution, air or nitrogen is now supplied via a feed line 13, a pressure builds up within the element which leads to the bending element activated in each case trying to produce the smallest possible volume with the smallest surface. Since the walling is inelastic no expansion can occur. It can be seen that in this way a curvature dependent on the geometrical shape of a bending element can be set, as is shown in FIG. 2. Depending on how the bending element is aligned, any bend can be implemented, with the activation of two adjacent bending elements also making a deflection at an intermediate angle possible.

FIG. 3 shows a cross-sectional view of a catheter 2, around the central catheter opening 14 of which, into which, for example, a further operational catheter, a signal or control line or an endoscopy device is introduced, six bending elements 12a-12f are arranged, offset radially outwards and symmetrically distributed in the example shown. Each bending element can be activated via a separate feed line not shown in any greater detail. The positioning and embodiment of the bending elements is in this case such that each bending element has its own preferred direction of bending, shown by the relevant arrows. The bending elements are offset radially outwards in relation to the longitudinal axis of the catheter and can either be positioned in segments, meaning that a number of bending elements are assigned to the same longitudinal position. Alternatively, it is also conceivable to position them offset radially outwards but overlapping each other, for example, as a type of spiral arrangement.

As FIG. 3 shows, each bending element is assigned a bending sensor 15a-15f. Each bending sensor 15a-15f is also connected via a separate signal line to the control device 5 and delivers a signal dependent on its shape. Each bending sensor performs a deformation of the catheter, so that on the basis of the given bending sensor signals, precise information about the local catheter shape and on the basis of the plurality of signals of the bending sensors also arranged over the length of the catheter and distributed around the longitudinal axis of the catheter, an exact image of the given actual shape of the catheter can be recorded. The sensors are locally permanently assigned to a specific bending element. As a result both the position of a bending element and of its assigned bending sensor relative to the longitudinal axis of the catheter are known to the control device 5.

FIG. 4 shows a basic sketch of an example for a deformation of a catheter 2 which can be achieved by separate activation of the bending elements. A plurality of bending elements 12, to each of which a bending sensor 15 is assigned, are arranged over the length of a part of the catheter. For the shape depicted, a total of six different bending points A, B, C, D, E and F are shown. To obtain the bending around the bending point A the bending element 12g is activated, the adjacent, especially opposite bending elements 12 remain unpressurized and thus flexible. To produce the bend around the point B the bending element 12h will be activated, for bending the catheter around the bending point C the bending element 12i will be activated. The procedure is the same to produce the bends around the bending point D (bending element 12j), E (bending element 12k) and F (bending element 12l). Obviously each bending sensor which is assigned to an activated bending element undergoes this bending with the element. This bending sensor and all the other bending sensors deliver the corresponding shape-related sensor signals to the control device 5, which can now calculate exactly the catheter shape depicted in FIG. 4.

The catheter device in accordance with the invention now allows an active self-propelled movement of the catheter in the vessel. The basic mode of operation is shown in FIGS. 5 and 6.

Figure 5:
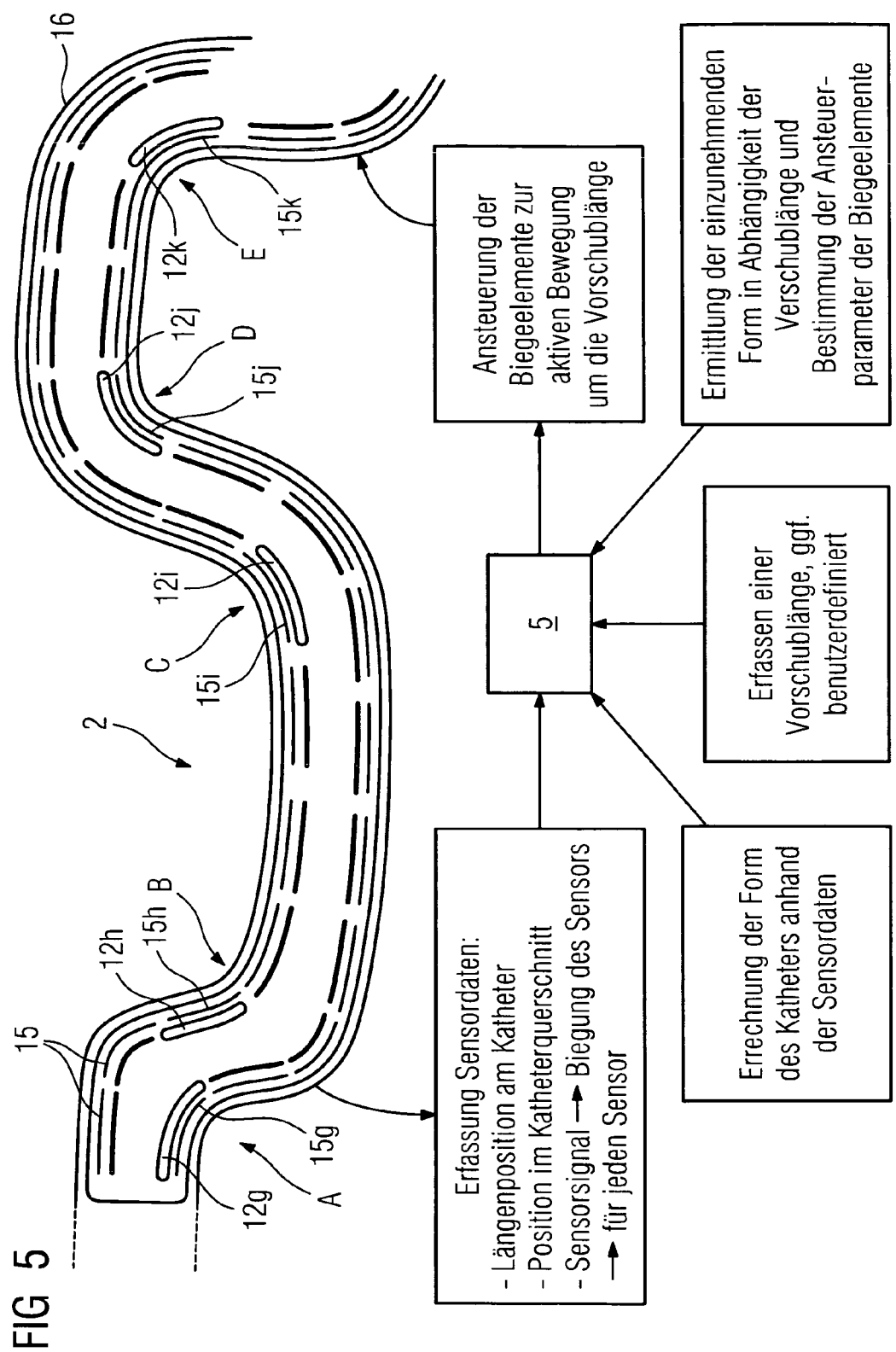

FIG. 5 shows a basic diagram of the catheter 2 deformed within a vessel 16 as a result of activation of a few bending elements. Shown in more detail there are five bending points A, B, C, D, E, with these bends having been produced by activation of the corresponding bending elements 12g, 12h, 12i, 12j and 12k on the side of the catheter.

Via the control device 5 the signals of all bending sensors 15 assigned to the individual bending elements 12 and thereby also of bending sensors 15g-15k assigned to bending elements 12g-12k are recorded. The control device 5 can now use these individual sensor signals to record the relevant bend or the degree of bending of the relevant bending sensor. For each bending sensor its longitudinal position on the catheter as well as its position in the catheter cross section is known to the control device. For example, each sensor can transmit a corresponding encoding in the sensor signal to enable it to be identified. On the basis of this local resolution it is now possible for each sensor signal to be assigned exactly to one point or to a short section of the catheter. From this knowledge the control device 5 is now in a position to determine the shape of the catheter on the basis of the sensor data. A data representation of the spatial position of the catheter or of its current geometrical shape can thus be recorded and for example continuously output on monitor 7.

In addition the control device 5 records a length of forward movement, where necessary user-defined, meaning that the user can, for example, define at keyboard 8 a forward movement that he requires which the catheter is to carry out independently. For example the user enters a length of 5 cm by which the catheter is to move itself forward in the subsequent movement step.

On the basis of the now known shape of the catheter, as well the defined length of forward movement, the shape to be assumed is now determined on the control device 5 side as a function of the length of forward movement, meaning that the necessary forward movement of the curves already formed in the catheter along the longitudinal axis taking account of the desired forward movement is determined. At the same time the activation parameters of the individual bending elements needed to perform the desired movement are determined. Based on these activation parameters the individual bending element is then activated for active movement by the length of forward movement.

In the exemplary embodiment shown the new shape to be assumed is shown in FIG. 6. To effect the active movement, in the exemplary embodiment shown the bending elements 12g', 12h', 12i', 12j' and 12k', which immediately follow the bending elements 12g-12k activated, that is actively bent starting from the actual position shown in FIG. 5 are activated while the bending elements 12g-12k, are depressurized. This activation causes a local deformation of the catheter in the area of the bending elements based on the determination of the activation parameters as a function of the desired forward movement. This curve, which causes a force to be exerted at a number of points on the vessel wall 16, meaning that the catheter supports itself or actively presses on the vessel wall 16. If all bending elements 12g'-12k' are essentially activated simultaneously, thereby also actively deformed with simultaneously depressurization of bending elements 12g-12k, the catheter actively presses itself forward in the vessel, thus pushing itself forward and undertakes a sort of crawling movement in conjunction with the vessel wall 16. The latter is slightly deformed hereby the pressure resulting from the deformation since it is not rigid. The change of shape can be recorded and checked via the signals of the bending sensors which are directly involved in the step described, namely sensors 15g-15k and 15g'-15k'.

Via control device 5 the activation of the bending element can now be calculated anew immediately after this active forward movement has been executed so that the catheter is essentially in a final shape corresponding to the starting position shown in FIG. 5, meaning one in which it corresponds as ideally as possible to the anatomy of the vessel. The continuous checking of the position or shape of the catheter can be undertaken by continuously recording the signals of the bending sensors, which means that the shape assumed by the catheter is always clear. The control device can thus continuously react to given situations and optimize the activation of the bending elements so that the catheter deviates as little as possible from the actual shape of the vessel or the organ.

For a new movement step, starting from the newly assumed actual shape of the catheter, as is shown in idealized form in FIG. 6, taking into consideration, for example, the length of forward movement already processed beforehand, new activation parameters are now calculated in order to move the catheter forward by a further distance increment, which in the ideal case corresponds to the forward movement length.

FIGS. 5 and 6 are simple basic diagrams which represent an idealized view of the active movement sequence. Since a vessel or an organ is not a rigid structure a forward movement in a movement step by exactly the defined length will not necessarily be possible, since the deformation of the bending element is always accompanied by a certain deformation of the vessel. As a result of the continuous recording of the actual catheter shape the control device can, however, taking into account the sensor signals, continuously transmit the optimized activation of the bending elements so that an independent catheter movement can be achieved and the catheter can almost move through the vessel by itself.

The invention claimed is:

1. A catheter device, comprising:
a non-segmented catheter for inserting into a hollow organ;
a plurality of internal, discrete and pressure activated flexural elements arranged parallel to and circumferentially around a longitudinal axis of the catheter in a ring like manner and distributed within the catheter and along a catheter length at a plurality of axial locations;
a control device for activating the flexural elements with regard to obtain a desired shape of the flexural elements; and
a plurality of bending sensors arranged parallel to and circumferentially around the longitudinal axis of the catheter in a ring like manner and arranged at a plurality of longitudinal locations along the catheter length, the bending sensors adapted to communicate with the control device, wherein
the flexural elements are adapted to be selectively activated for obtaining the desired shape and to bend the catheter off-axis of the longitudinal axis and form a smooth radius of the catheter using the control device, the control device adapted to:
determine a current geometrical shape of the catheter using bending signals supplied by the bending sensors; and
determine a required change of shape of the flexural elements for causing a desired movement of the catheter so that the catheter is at least partially movable inside the hollow organ by selectively applying a force to an inner organ wall of the hollow organ using flexural elements activated according to the required change of shape.

2. The catheter device according to claim 1, wherein the hollow organ is a blood vessel.

3. The catheter device according to claim 1, wherein all flexural elements necessary to obtain the desired movement of the catheter are simultaneously activated by the control device.

4. The catheter device according to claim 1, further comprising an input device for inputting a forward movement length related to the desired movement of the catheter.

5. The catheter device according to claim 4, wherein the forward movement length is a value relative to a metric or non-metric length unit.

6. The catheter device according to claim 4, further comprising a recording device for recording a movement of the catheter, wherein
the desired forward movement is executed by moving the catheter manually; and the forward movement length corresponding to the desired forward movement is determined by the recording device.

7. The catheter device according to claim 6, wherein the forward movement length is a total movement length covered by the catheter within a specified time interval.

8. The catheter device according to claim 6, wherein the forward movement length is a mathematically integrated movement speed of the catheter relative to a specified time interval.

9. The catheter device according to claim 4, wherein the control device is adapted to successively activate the flexural elements several times for obtaining the desired shape of the flexural elements using the forward movement length input several times.

10. The catheter device according to claim 1, wherein the control device is adapted to activate the flexural elements such that, after a movement of the catheter, the flexural elements recover their shape as it was before the movement of the catheter.

11. A catheter device, comprising:
a non-segmented catheter having a longitudinal axis for insertion into a hollow organ;
a plurality of internal and discrete fluidically activated flexural elements coaxially arranged around the longitudinal axis of the catheter at a plurality of locations along the catheter longitudinal axis, diametrically opposed ones of the flexural elements at a particular location comprising differing lengths configured to bend the catheter off-axis of the longitudinal axis and to provide asymmetrical movement of the catheter upon inflation of the opposed ones of the flexural elements;
a control device for controlling inflation of the flexural element to obtain a desired shape of the catheter; and
a plurality of bending sensors coaxially arranged around the longitudinal axis of the catheter at a plurality of locations along the catheter length, the bending sensors adapted to communicate with the control device to indicate an actual shape of the catheter.

* * * * *